United States Patent [19]
Pepper et al.

[11] Patent Number: 6,039,813
[45] Date of Patent: *Mar. 21, 2000

[54] FRUCTOSE-BASED GRANULATED PRODUCT AND A PROCESS FOR THE PRODUCTION THEREOF

[75] Inventors: Tammy Pepper, Twickenham, United Kingdom; Christof Krüger, Hamburg, Germany; Matti Mäkelä, Kirkkonummi, Finland

[73] Assignee: Xyrofin OY, Kotka, Finland

[ * ] Notice: This patent issued on a continued prosecution application filed under 37 CFR 1.53(d), and is subject to the twenty year patent term provisions of 35 U.S.C. 154(a)(2).

[21] Appl. No.: 07/777,347
[22] PCT Filed: Jun. 5, 1990
[86] PCT No.: PCT/FI90/00152
    § 371 Date: Jan. 15, 1992
    § 102(e) Date: Jan. 15, 1992
[87] PCT Pub. No.: WO90/14821
    PCT Pub. Date: Dec. 13, 1990

[30] Foreign Application Priority Data

Jun. 7, 1997 [FI] Finland .................. 89/2797

[51] Int. Cl.⁷ ...................................... B29C 1/04
[52] U.S. Cl. .................. 127/42; 106/213; 106/214
[58] Field of Search ............. 127/42; 106/213, 106/214; 426/72, 548, 658; 514/23

[56] References Cited

U.S. PATENT DOCUMENTS

| | | | |
|---|---|---|---|
| 3,627,583 | 12/1971 | Troy et al. | 127/29 |
| 3,684,573 | 8/1972 | Voigt et al. | 127/63 |
| 4,007,052 | 2/1977 | Heinemann et al. | 127/63 |
| 4,698,101 | 10/1987 | Koivurinta | 127/29 |
| 5,536,526 | 7/1996 | Virtanen et al. | 426/658 |
| 5,616,361 | 4/1997 | Virtanen et al. | 426/658 |

*Primary Examiner*—Mark L. Bell
*Assistant Examiner*—Patricia L. Hailey
*Attorney, Agent, or Firm*—Kenyon & Kenyon

[57] ABSTRACT

The invention relates to a predominantly fructose-based granulated product suitable for use in the manufacture of tablets by direct compression means and consisting of free-flowing granules comprising about 92% to about 98% by weight of fructose, about 1% to about 7% by weight of a physiologically acceptable polyol selected from sorbitol, maltitol, lactitol, xylitol, mannitol, isomalt and mixtures thereof, op-tionally with other hydrogenation products of sugars, and less than about 1% by weight of water. The granu-lated product is produced according to the invention by agglomerating crystalline fructose ground to a fine particle size by means of an aqueous solution of the polyol, while the fructose is brought to a rapid movement to form a granular product, and drying the granules by means of dry air to a water content of less than 1%.

35 Claims, 2 Drawing Sheets

FRUCTOSE-BASED GRANULATED PRODUCT AND A PROCESS FOR THE PRODUCTION THEREOF

This invention relates to a granulated product which is suitable for use in the manufacture of tablets by direct compression means and which contains fructose and a minor amount of a physiologically acceptable polyol, and to a process for the production thereof.

Direct compression techniques have become increasingly popular in tablet manufacturing in the pharmaceutical and food industries. A good material for use in direct compression techniques should be free-flowing, it should not get cloddy or lumpy and it should form firm and hard tablets with a reasonable compression force.

Many ingredients used in tablets are, as such, not suited for direct compression due to their insufficient flowability and/or compressibility. Therefore, binding and diluting agents suited for direct compression have been developed, which may also function as, e.g., flavour improving agents.

Sweet carbohydrates such as sugars and sugar alcohols are suitable for use as raw materials of tablets as binding and diluting agents for other active ingredients (e.g. pharmaceuticals) or as the major component of tablets (e.g. confectionery or energy tablets) because of their pleasant taste. However, most crystalline sugars and sugar alcohols as such are poorly suited for direct compression techniques, since as crystals they do not form tablets, and powders prepared therefrom are very poorly flowable. Therefore, various granulated products of sugars and sugar alcohols have been developed for use in direct compression. In the pharmaceutical and food industries, these products can be regarded as semifinished products which are utilized as raw materials in effective tableting techniques.

Examples for commercial binding and diluting agents include EMDEX, which is an agglomerated dextrose; DIPAC, which is an agglomerated sucrose containing dextrins; and STARCH 1500, which is pre-gelatinized directily compressible starch and mannitol. U.S. Pat. No. 4,352,821 discloses a product consisting of fructose and a salt. U.S. Pat. No. 4,159,345 discloses an excipient prepared from microcrystalline cellulose.

Fructose has several advantages as a raw material of tablets. The taste is sweet, it is suitable for diabetics and the water solubility thereof is good. Agglomeration of fructose to a directly compressible product, however, presents problems.

Fructose granules agglomerated from a water solution are hard and the compressibility is unsatisfactory. A granular fructose product has been prepared also from a fructose-alcohol mixture; for example, see U.S. Pat. No. 3,684,573. The use of alcoholic solutions, however, calls for special precautions in industrial applications. It is therefore a great advantage if a compressible product can be prepared using only water as solvent. According to European Patent Application published with No. 0036738, such a product can be prepared by adding a comparatively large amount of dextrins to a fructose solution and spray-drying the mixture. This method does not provide a product that is predominantly fructose, but rather a sugar mixture including fructose as one of several carbohydrates. Furthermore, U.S. Pat. No. 4,698,101 discloses a fructose-based binding and diluting agent, namely a fructose agglomerate, suited for use in direct compression tableting techniques. This agglomerate contains in combination with fructose about 2% to about 20% by weight of a disaccharide, preferably maltose, wherefore it is unsuitable for diabetics.

The object of the present invention is to provide an essentially fructose-based granular product having flowability and compressibility characteristics which make it suitable for the manufacture of tablets by direct compression techniques, and which is suitable also for diabetics.

This object is achieved according to the present invention with a granulated product which consists of free-flowing granules comprising about 92% to about 98% by weight of fructose, about 1% to about 7% by weight of a physiologically acceptable polyol selected from sorbitol, maltitol, lactitol, xylitol, mannitol, isomalt and mixtures thereof, optionally with other hydrogenation products of sugars, and less than about 1% by weight of water. In a particularly preferred embodiment, the product of the present invention comprises about 95% to about 97% by weight of fructose, about 3% to about 5% by weight of the polyol, and less than about 0.5% by weight of water.

Figure 1:
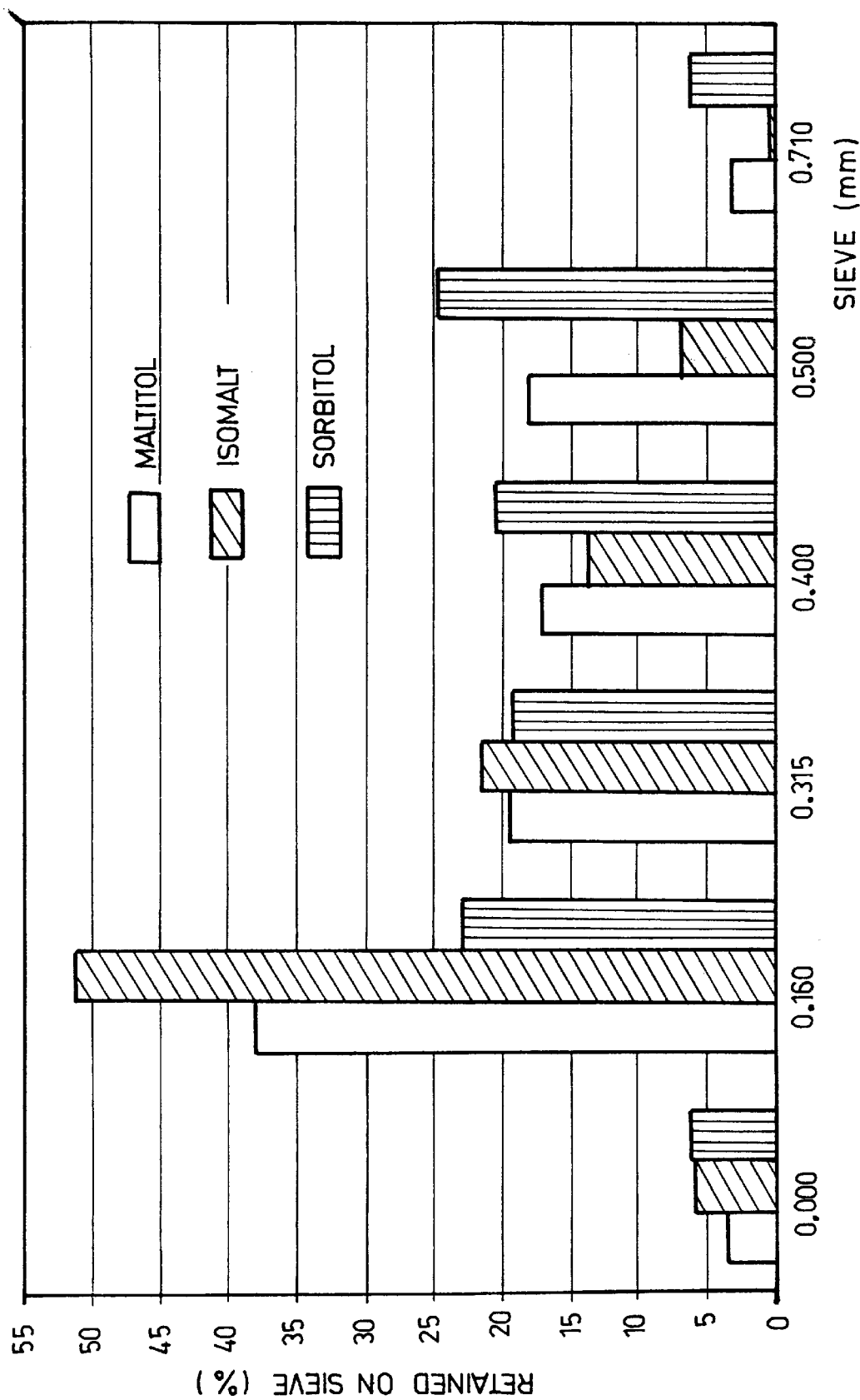
FIG. 1 is a graph showing the sieve analysis for the products produced in Examples 1, 3, and 4.

Preferably, the bulk density (loose density, LD) of the product of the present invention is between 0.45 g/cm$^3$ and 0.80 g/cm$^3$, and the average particle size is between 0.25 mm and 0.55 mm.

The granulated product of the present invention has good flow properties and it can be directly compressed with reasonable compression forces to form tablets having a high crushing strength and advantageous solubility properties. This granulated product can be used in the food industry, e.g., as a major component in so called energy tablets or confectionery tablets, as well as in the pharmaceutical industry, e.g. as a binder, diluting agent and/or flavour improving agent in vitamin tablets, mineral tablets and with other pharmacologically active substances both medicinal and non-medicinal. It is also possible that the granulated fructose product of the present invention will be used as a binder/diluting agent in tablets pressed from intensive sweeteners (e.g. saccharin, aspartame, acesulfame K, cyclamate, alitame, sucralose).

The present invention also provides a process for the production of a predominantly fructose-based granulated product suitable for the manufacture of tablets by direct compression, said process comprising the steps of agglomerating finely ground crystalline fructose with an aqueous solution of a physiologically acceptable polyol selected from sorbitol, maltitol, lactitol, xylitol, mannitol, isomalt and mixtures thereof, optionally with other hydrogenation products of sugars, while bringing the fructose to a rapid movement to form a granular product, and drying the granules by means of dry air to a water content of less than 1% by weight, the amount of the aqueous solution of the polyol being selected so that the dried granular product comprises fructose and the polyol at the levels defined above.

The flowability of a granular product can be measured by allowing a sample (200 g) to flow through a funnel (runner pipe: diameter 7 mm; length 25 mm) on to a balance connected to a recording device. The flowability (sec./100 g) of the substance can be calculated from the curve so obtained. Another procedure for evaluating flowability is the determination of angle of repose: a sample (50 g) is passed slowly through a funnel on to a paper, and the angle defined by the mound so formed and the paper is measured.

The bulk density of a substance can be determined by measuring a volume of exactly 300 ml into a measuring cylinder. The sample is weighed accurately. The loose density (LD) can be calculated from these data. Thereafter the sample is vibrated at an amplitude of 1.5 mm, until it does not pack to a smaller volume. The volume is recorded, and the bulk density (tapped density, TD) is calculated.

Fructose used as raw material in the production of the granulated product of the present invention has preferably a purity exceeding 98% by weight, and has been ground to an average particle size of below 200 μm by means of a suitable mill, such as a hammer mill common in the sugar industry to produce icing sugar.

The physiologically acceptable polyol is added to the fructose powder at the granulation stage in the form of an aqueous solution. This may contain a single pure polyol or a mixture of polyols. For instance, commercial products produced by hydrogenation of sugars may be used, such as isomalt, which is sold under trade name Palatinit (a 1:1 mixture of α-D-glucopyranosyl( 1→6)mannitol and α-D-glucopyranosyl-(1→6)sorbitol), or maltitol syrup available under trade name Finmalt L (manufactured by Suomen Xyrofin Oy, Kotka, Finland) containing 75% by weight of dry substance wherefrom 62% to 70% is maltitol, max. 8.0% is sorbitol and 22% to 37% is other hydrogenated saccharides. The polyol is added to the fructose powder by spraying in the form of an aqueous solution having a dry substance content suitable for the granulation device used. The nozzle structure of, for instance, the Schugi device (high shear mixer/fluidized bed drier combination) requires a dry substance content below 35%, while e.g. in a fluidized bed granulator more concentrated solutions can be used, such as solutions having a polyol content of about 70% by weight.

The fructose-based product of the present invention is prepared by granulating the ground fructose together with a small amount of the polyol solution by means of a suitable granulation device. The product is dried rapidly in a fluidized bed, for instance. The drier may be separate, or the drying may be carried out in the granulator, depending on the type of device. In the granulation device, the ground fructose and the polyol solution added evenly thereto are brought into a rapid movement which effects the agglomeration of the ground fructose with a small amount of the polyol solution. The grain size can be controlled by adjusting the mixture ratios, the mixing efficiency or the concentration of the agglomerating solution.

The granulated product is dried rapidly e.g. in a fluidized bed by means of dry air so that the final moisture content is below about 1% by weight, preferably below 0.5% by weight. The average particle size is between 0.25 mm and 0.55 mm.

The granulates prepared using the polyols defined above have very similar properties. The type and the size of the apparatus used in the production, however, have an influence on the properties of the product; thus, e.g. a granulate produced in the industrial scale differs to some extent from that produced in the laboratory scale.

The product obtained according to the invention is a freely flowing granular product which has excellent compressibility and which withstands storing without getting cloddy. Preferably it has the following properties:

| | |
|---|---|
| Moisture content (after drying) | less than 0.5% by weight |
| Average particle size | 0.25 mm to 0.50 mm |

-continued

| | |
|---|---|
| Fructose | about 95% to about 97% by weight |
| Polyol | about 3% to about 5% by weight |
| Bulk density (LD) | 0.45 g/ml to 0.55 g/ml |
| Flowability | max. 15 sec./100 g |

Some details of the present invention are presented in the following examples, which are merely illustrative for the invention and should not be considered restrictive to the scope of the invention.

EXAMPLE 1

The powdered fructose used in the trials was Fructofin CM made by Suomen Xyrofin Oy, Kotka, Finland. Its purity is 99.5% minimum and average particle size 170 microns. The batch size used for one granulation trial was 500 g of fructose which was loaded into a lab scale fluidized bed granulator (Aeromatic by Aeromatic Ltd., Budendorf, Switzerland). A 70% aqueous solution of sorbitol was used as an agglomerating solution. The liquid flow to the granulator was 2.4 to 3.6 ml/minute. The drying air temperature was 50° C. and the pressure of atomizing air was 1.5 to 2 bar. The spray nozzle was in its uppermost position. The amount of sorbitol solution used was 20 ml/500 g. The final concentration of sorbitol in the product, calculated on a dry substance basis, was 3.2%. The granulate was dried in the fluidized bed until it seemed to be free-flowing. Drying was continued in an oven at 50° C. over-night to a final moisture content of 0.3%.

| | |
|---|---|
| Fructose | 96.5% |
| Sorbitol | 3.2% |
| Water | 0.3% |

The bulk density and the flowability data are shown in the following Table 1; the sieve analysis as a graph in FIG. 1.

EXAMPLE 2

The conditions for the granulator were as described in Example 1. The agglomerating solution was a 70% lactitol solution which was used in an amount of 20 ml for a batch of 500 g. The lactitol concentration in the final product was 3.2% on a dry substance basis. Final drying was made in an oven to a moisture content of 0.3%.

The bulk density and the flowability data are shown in the following Table 1.

EXAMPLE 3

The conditions for the granulator were as described in Example 1. The agglomerating solution was a 70% solution of isomalt and it was used in an amount of 40 ml/500 g. The isomalt concentration in the product was 6.3% on a dry substance basis. The product was dried as described above.

The bulk density and the flowability data are shown in Table 1; the sieve analysis as a graph in FIG. 1.

EXAMPLE 4

The conditions for the granulator were as described in Example 1. The agglomerating solution was a 70% solution of maltitol and it was used in an amount of 20 ml/500 g. The maltitol concentration in the product was 3.2% on a dry substance basis. The product was dried as described above.

The bulk density and the flowability data are shown in Table 1; the sieve analysis as a graph in FIG. 1.

EXAMPLE 5

The conditions for the granulator were as described in Example 1. The agglomerating solution was a 70% solution of xylitol and it was used in an amount of 30 ml/500 g. The xylitol concentration in the product was 4.8% on a dry substance basis. The product was dried as described above.

The bulk density and the flowability data are shown in Table 1.

EXAMPLE 6

The conditions for the granulator were described in Example 1. The agglomerating solution was a 30% solution of mannitol and it was used in an amount of 50 ml/600 g. The mannitol concentration in the product was 2,4% on a dry substance basis. The product was dried as described above.

The bulk density and the flowability data are shown in Table 1.

EXAMPLE 7

Figure 2:
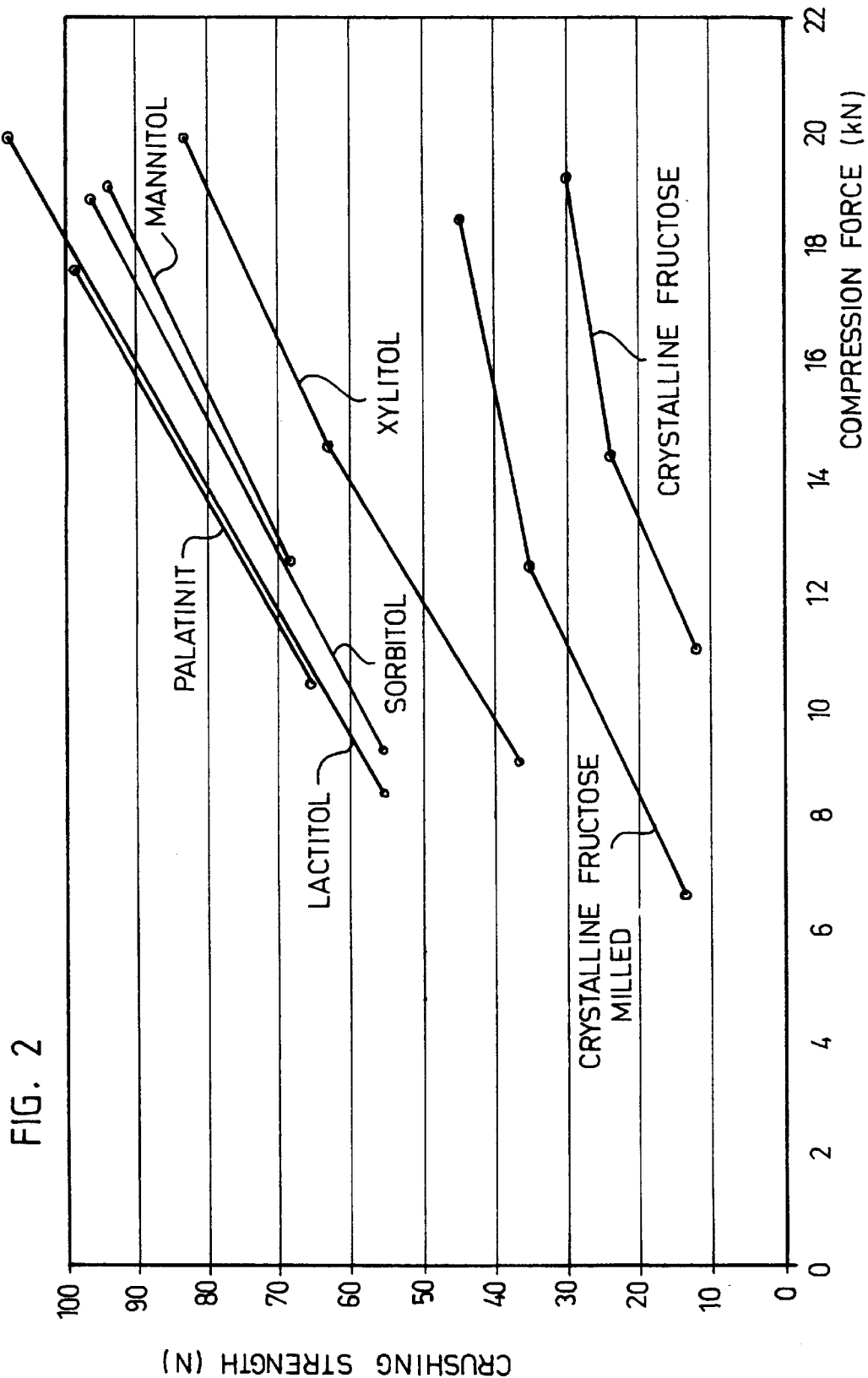
FIG. 2 is a graph showing the crushing strengths of the tablets prociticed in Example 7.

The granulates produced according to examples 1 to 6 were compressed to tablets by means of an eccentric press (Korsch EK-O/DMS, Korsch OHC Maschinenfabrik, Berlin, West Germany). Magnesium stearate (1%) was used as an additive. The diameter of the tablets was 11 mm and the weight 500 mg. The crushing strength of tablets manufactured with different compression forces was determined in accordance with the standard methods in pharmaceutical industry using a Schleuniger 2E crushing strength tester; the results are shown graphically in FIG. 2 (crushing strength versus compression force). Crushing strengths of tablets pressed from crystalline fructose and powdered fructose as such are also shown in FIG. 2 for comparison. The friability of the tablets measured using a Roche-friabilator is shown in Table 1.

The granulates prepared according to Examples 1 to 6 can be compressed to tablets having compositions illustrated in Examples 8 to 11.

EXAMPLE 8

| Confectionery tablet | |
|---|---|
| | g/1000 tablets |
| Fructose granulate | 1440.0 |
| Citric acid | 43.5 |
| Magnesium stearate | 7.5 |
| Lemon flavour (Firmenich 51.421/AP 05.51) | 7.5 |
| Lake colour (Quinoline yellow) | 1.5 |
| | 1500.0 |

EXAMPLE 9

| Vitamin C tablet | |
|---|---|
| | g/1000 tablets |
| Fructose granulate | 414.5 |
| Ascorbic acid | 30.0 |
| Sodium ascorbate | 45.0 |
| Citric acid | 2.0 |
| Magnesium stearate | 5.0 |
| Orange flavour (Firmenich 55.604/TP 05.51) | 3.0 |
| Lake colour (Sunset yellow) | 0.5 |
| | 500.0 |

EXAMPLE 10

| Multivitamin tablet | |
|---|---|
| | g/1000 tablets |
| Fructose granulate | 730.043 |
| Ascorbic acid | 30.0 |
| Niacin | 12.0 |
| Pantothenic acid | 4.6 |
| Vitamin E | 2.0 |
| Riboflavin | 1.6 |
| Thiamin | 1.2 |
| Vitamin B6 | 1.0 |

TABLE 1

The properties of fructose/polyol granulates and the friability of tablets produced thereof

| | The granulate prepared in Example | | | | | |
|---|---|---|---|---|---|---|
| | 1 | 2 | 3 | 4 | 5 | 6 |
| Bulk density (LD), g/ml | 0.516 | 0.536 | 0.622 | 0.592 | 0.601 | 0.61 |
| Flowability (7 mm orifice) sec./100 g | 13.5 | 11.0 | 9.2 | 10.6 | 12.9 | 25.0 |
| angle of repose, degrees | 30–35 | 36–38 | 38–42 | 28–32 | 30–35 | 38–42 |
| Friability % loss weight *) | 0.77 | 6.2 | 8.3 | 2.16 | 0.7 | 0.6 |

*)Compression force range 17.5–19.5 kN, tablets 500 g, diameter 11 mm, flat faced bevelled edges.

-continued

Multivitamin tablet

| | g/1000 tablets |
|---|---|
| Vitamin A | 0.75 |
| Vitamin D | 0.005 |
| Vitamin B12 | 0.002 |
| Magnesium stearate | 8.0 |
| Strawberry flavour (Firmenich 52.166/AP 05.51) | 8.0 |
| Lake colour (Ponceau 4R) | 0.8 |
| | 800.0 |

EXAMPLE 11

Energy tablet

| | g/1000 tablets |
|---|---|
| Fructose granulate | 1980.0 |
| Magnesium stearate | 20.0 |
| | 2000.0 |

We claim:

1. A predominantly fructose-based granulated product suitable for use in the manufacture of tablets by direct compression means, comprising free-flowing granules comprising about 92% to about 98% by weight of fructose, about 1% to about 7% by weight of at least one of a physiologically acceptable polyol selected from the group consisting of sorbitol, maltitol, lactitol, xylitol, mannitol and isomalt and less than about 1% by weight of water, wherein the granulated product is produced while bringing fructose particles to a rapid movement in air.

2. The granulated product of claim 1, wherein the product comprises about 3% to about 5% by weight of said polyol.

3. The granulated product of claim 2 wherein said polyol is sorbitol.

4. The granulated product of claim 2 wherein said polyol is lactitol.

5. The granulated product of claim 2 wherein said polyol is isomalt.

6. The granulated product of claim 2 wherein said polyol is mannitol.

7. The granulated product of claim 1 wherein said polyol is sorbitol.

8. The granulated product of claim 1 wherein that said polyol is lactitol.

9. The granulated product of claim 1 wherein said polyol is isomalt.

10. The granulated product of claim 1 wherein said polyol is mannitol.

11. The granulated product of claim 1 wherein the average particle size thereof is between 0.25 mm and 0.55 mm.

12. A confectionery tablet or energy tablet comprising the granulated product according to claim 1.

13. A vitamin tablet, mineral tablet or other tablet containing a pharmacologically active substance comprising the granulated product according to claim 1.

14. A intensive sweetener tablet comprising the granulated product according to claim 1.

15. The granulated product of claim 1 further comprising a second polyol.

16. A tablet comprising the granulated product of any one of claims 7 to 11.

17. A tablet prepared by direct compression of the granulated product of claim 11.

18. The tablet of claim 17 which further comprises magnesium stearate.

19. The tablet of claim 17 wherein the polyol included in said granulated product is sorbitol.

20. The tablet of claim 17 wherein the polyol included in said granulated product is lactitol.

21. The tablet of claim 17 wherein the polyol included in said granulated product is isomalt.

22. The tablet of claim 17 wherein the polyol included in said granulated product is mannitol.

23. The tablet of claim 17, further comprising a performance-enhancing effective amount of an active ingredient selected from trace elements, vitamins and other pharmacologically active substances.

24. The tablet of claim 17, further comprising an intensive sweetener.

25. The tablet of claim 17, further comprising flavour or color improving agents.

26. The granulated product of claim 1 wherein the product is capable of withstanding storage without becoming cloddy.

27. The granulated product of claim 1 wherein granulation is by fluid bed granulation.

28. The granulated product of claim 1 wherein the product is produced by agglomerating crystalline fructose ground to a fine particle size with an aqueous solution of the physiologically acceptable polyol while the fructose is brought to a rapid movement in air, and drying the granules by means of dry air to a water content of less than 1%.

29. A process for preparing a predominantly fructose-based granulated product which is suitable for use in direct compression tableting, comprising the steps of:

agglomerating crystalline fructose ground to a fine particle size with an aqueous solution of at least one physiologically acceptable polyol selected from the group consisting of sorbitol, maltitol, lactitol, xylitol, mannitol and isomalt while bringing said crystalline fructose to a rapid movement in air to form a granular product; and drying said granular product by means of dry air to a water content of less than 1%, wherein the amount of said polyol solution is selected so that the dried product contains about 92% to about 98% by weight of fructose and about 1% to about 7% by weight of said polyol.

30. The process of claim 29 further comprising the steps of:

adding a second polyol during the agglomerating step.

31. The process of claim 29 wherein drying is performed in a fluidized bed.

32. The process of claim 29 wherein the product is capable of withstanding storage without becoming cloddy.

33. The process of claim 29 wherein granulation is by fluid bed granulation.

34. A process for preparing a predominately fructose-based, free-flowing granulated product which is suitable for use in direct compression tableting, consisting essentially of:

(i) agglomerating crystalline fructose ground to a fine particle size with an aqueous solution of at least one physiologically acceptable polyol selected from the group consisting of sorbitol, maltitol, lactitol, xylitol, mannitol and isomalt while bringing the fructose to a rapid movement in air to form a granular product; and (ii) drying said granular product by means of dry air to a water content of less than 1%, wherein the amount of said polyol solution is selected so that the dried product contains about 92% to about 98% by weight of fructose and about 1% to about 7% by weight of said polyol.

35. A predominately fructose-base granulated product suitable for use in the manufacture of tablets by direct compression means, comprising free-flowing granules comprising about 92% to about 98% by weight of fructose, about 1% to about 7% by weight of at least one of a physiologically acceptable polyol selected from the group consisting of sorbitol, maltitol, lactitol, xylitol, mannitol and isomalt and less than about 1% by weight of water; wherein said free-flowing, granulated product is prepared by a process consisting essentially of:

(i) agglomerating crystalline fructose ground to a fine particle size with an aqueous solution of at least one physiologically acceptable polyol selected from the group consisting of sorbitol, maltitol, lactitol, xylitol, mannitol and isomalt while bringing the fructose to a rapid movement in air to form a granular product; and (ii) drying said granular product by means of dry air to a water content of less than 1%.

* * * * *